United States Patent [19]

Cotner et al.

[11] Patent Number: 5,645,054
[45] Date of Patent: Jul. 8, 1997

[54] DEVICE AND METHOD FOR THE TREATMENT OF SLEEP APNEA SYNDROME

[75] Inventors: Ronald L. Cotner, Derry; Gerald J. Parise, Bedford; Thomas E. Asacker, Exeter, all of N.H.; Bijan Sadrnoori, N. Andover, Mass.; Robert A. Muller, Manchester, N.H.

[73] Assignee: SleepNet Corp., Manchester, N.H.

[21] Appl. No.: 331,030

[22] Filed: Oct. 27, 1994

Related U.S. Application Data

[63] Continuation-in-part of Ser. No. 184,976, Jan. 24, 1994, abandoned, which is a continuation-in-part of Ser. No. 890,815, Jun. 1, 1992, abandoned.

[51] Int. Cl.[6] .......................... A61M 16/00; A62B 7/00; F16K 31/02
[52] U.S. Cl. ................... 128/204.23; 128/204.21; 128/204.26; 128/205.25
[58] Field of Search .................. 128/204.23, 204.26, 128/205.25, 207.18, 716, 719, 204.21

[56] References Cited

U.S. PATENT DOCUMENTS

| | | | |
|---|---|---|---|
| 4,537,190 | 8/1985 | Caillot et al. | 128/204.22 |
| 4,570,631 | 2/1986 | Durkan | 128/204.23 |
| 4,655,213 | 4/1987 | Rapoport et al. | 128/205.25 |
| 4,803,471 | 2/1989 | Rowland | 340/626 |
| 5,117,819 | 6/1992 | Servidio et al. | 128/204.18 |
| 5,148,802 | 9/1992 | Sanders et al. | 128/204.18 |
| 5,174,287 | 12/1992 | Kallok et al. | 128/419 |
| 5,199,424 | 4/1993 | Sullivan et al. | 128/204.18 |
| 5,239,995 | 8/1993 | Estes et al. | 128/204.23 |
| 5,245,995 | 9/1993 | Sullivan et al. | 128/204.23 |
| 5,313,937 | 5/1994 | Zdrojkowski | 128/202.23 |
| 5,335,654 | 8/1994 | Rapoport | 128/204.23 |
| 5,353,788 | 10/1994 | Miles | 128/204.23 |

FOREIGN PATENT DOCUMENTS

WO8203548 11/1982 WIPO ..................... 128/204.23

OTHER PUBLICATIONS

R.W. Southworth et al; *Digital Computation and Numerical Methods*, pp. 6–10.

R.D. Ballard, MD. et al *Sleep Apnea; Diagnosis and Treatment* The Western Journal of Medicine pp. 248–250.

C. Guilleminault et al; *Unattended CPAP Titration: Toward A Smart Machine*: Sleep Research 21, 1982 pp. 2342–2352.

D. M. Rapoport, M.D.; *Reversal of the "Pickwickian Syndrome" by Long Term Use of Nocturnal Nasal Air Press*. New Eng. Journ. Med. 307:931–933 Oct. 7, 1982.

C. B. Sullivan; *Reversal of Obstructive Sleep Apnea by Contin. Posit. Airway Press. Appl'd through The Nares* The Lancet May 18, 1981 pp. 862–865.

A. R. Schwartz et al: *Induction of Upper Airway Occlusion in Sleeping Indiv. w/Subatmos. Nasal Press* 0161-7567/88 The American Physiological Soc. pp. 535–542.

S. M. Garay, M.D.: *Therapeutic Options for Obstructive Sleep Apnea*: Respiratory Management Jul./Aug. 87 pp. 11–15.

D. M. Rapoport, M.D.: *Techniques for Administering Nasal CPAP* 1987 by Brentwood Pub.

(List continued on next page.)

*Primary Examiner*—Kimberly L. Asher
*Attorney, Agent, or Firm*—Testa, Hurwitz & Thibeault, LLP

[57] ABSTRACT

The present invention comprises a method and apparatus for the treatment of sleep apnea through the application of real-time, interactive positive airway pressure within the airway of a patient attached to the system. A single sensor is arranged in fluid communication with the airway of the air delivery conduit, and is designed to detect abnormal inspiratory flow to the patient's airway on a single breath basis. Output air pressure from the air source to the airway of the patient is continuously increased, instantaneously stopped, and slowly decreased in response to real-time changes in the patient's inspiratory flow curve detected and interpreted by this apparatus, thus providing the optimal pressure required to restore airway patency on each breath.

11 Claims, 3 Drawing Sheets

OTHER PUBLICATIONS

*Process Instruments & Automatic Analysis* Chap. 31, pp. 897–900 & 919–930.

A. Cohen, PhD; *Biomedical Signal Processing*, vol. II Compression and Automatic Recognition pp. 1–18.

Remmers, JE; *Mechanics of the Pharynx in Patients w/Obstructive Sleep Apnea*: Sleep and Respiration pp. 261–271; 1990– Wiley Liss. Inc.

M.H. Sanders et al: *Obstruct. Sleep Apnea Trtd by Indep. Adjust. Inspiratory and Expir. Pos. Airway Press. via Nasal Mask* Physiol. & Clinical Implic. pp. 317–324.

M.C. Demirozu et al; *A Comparison of 9 Nasal CPAP Machines in Maintaining Mask Pressure During Simulated Inspiration;* Sleep 14(3):259–262 1991 Assoc. Prof. Sleep Soc.

R. P. Hollman, MD., et al: *A Home Monitoring System for CPAP:* Chest vol. 93 pp. 730–733 Apr. 1988.

Charles G. Alex et al; *Effects of CPAP on Upper–Airway and Respir. Muscle Activity* pp. 2026–2030, The American Phys. Soc.

A. K., Mahadevia; *Effects of Expir. Pos. Airway Press. on Sleep Induced Respir. Abnorm. in Patients w/Hypersomnia Sleep Apnea Syndrome* pp. 708–711 Am. Rev Respin Dis, 1983; 128; 708–711.

R. Douglas McEvoy et al; *Treatment of Obstruct. Sleep Apnea Syndrome w/Nasal CPAP;* Sleep 7(4): 313–325, 1994 Raven Press, N.Y.

M.H. Sanders, MD. et al; *CPAP via Nasal Mask; A Treatment for Occlusive Sleep Apnea* pp. 144–145; Chest/83/1/ Jan., 1983.

Literature of Respiratory Facts and Physiologic Monitoring pp. 30–45.

Diane Blodgett; Manual of Respiratory Care Procedures 2nd Ed. pp. 220–281.

J. J. Carr; *Biomedical Equip. Use, Maintenance and Management* pp. 6, 7 & 328.

R. Pollack et al.; *Improved Technique for Recording Respiratory Data* pp. 541–544 & 547, Med & Biol Eng. & Comput, 1977, 15.

Literature of Healthdyne Technol. Exhib. A–C Entitled *SleepTalk*, vol. III Issue 1, Winter 1991.

Literature entitled: *Sullivan™ Nasal CPAP System*, Exhibit 1 May, 1990, ©ResCare Limited.

Literature entitled: *Opening a New Window on CPAP Therapy*, Medtronic, 1991 (VC9101 322EN).

Literature entitled: *Sullivan CPAP APD2*, Res Care Ltd., PCT/AU88/00215.

Literature entitled: *Multiple Choice*, Respironics, 1991.

Literature entitled: *Sleep It Places Unattended Sleep Testing In Your Hand*, CNS, Inc.

Literature by Laboratory Software: *Clinical Tests using Self–Setting CPAP Device* pp. 2–10, Oct. 9, 1991.

C. B. Spearman et al; *The New Generation of Mechanical Ventilators;* Respiratory Care Jun. '87 vol. 32 No. 6 pp. 403–418.

Literature by Healthdyne Tech; *Tranquility Nasal CPAP System*, 1988.

Literature by Y.G. Dupuis; *Ventilators, Theory and Clinical Application;* 1986 pp. 107–117.

DEVICE AND METHOD FOR THE TREATMENT OF SLEEP APNEA SYNDROME

This is a continuation-in-part application of U.S. patent application Ser. No. 08/184,976 filed Jan. 24, 1994, now abandoned, which is a continuation-in-part application of U.S. patent application Ser. No. 07/890,815, filed Jun. 1, 1992, now abandoned, which are all incorporated herein by reference, in their entireties.

BACKGROUND OF THE INVENTION

1. Field of the Invention

This invention relates to treatment of sleep apnea syndrome and more particularly to an arrangement of treating a patient with ventilation to overcome critical flow limitations created by insufficient inspiratory effort, obstruction, blockage, narrowing, or constriction of a patient's airway.

2. Prior Art

The present invention relates to the treatment of sleep apnea syndrome, a disorder characterized by repetitive episodes of partial or complete upper airway obstruction during sleep. Hundreds of apneic episodes may occur during the sleep period, and are usually associated with blood oxygen desaturation and subsequent arousal from sleep. Consequences of sleep apnea syndrome include: social problems due to snoring, excessive daytime sleepiness, increased accidents due to sleepiness, and severe blood oxygen desaturation which may lead to the development of cardiopulmonary problems, including sudden death during sleep.

Since the early 1980's, an effective and commonly used treatment for sleep apnea syndrome has been Continuous Positive Airway Pressure (CPAP). CPAP consists of a positive pressure air supply delivered to a patient by means of a sealed breathing mask. Without positive air pressure therapy, the tissues in the upper airway collapse due to negative inspiratory pressure, thereby producing obstruction. The continuous positive airway pressure provides an air splint to the upper airway, thereby preventing collapse of the pharyngeal tissues.

CPAP devices provide a preset flow of air with a pressure between two and twenty centimeters of water, to prevent this suction collapse of the tissue. The CPAP device is preset at the highest pressure required to prevent the patient's most severe degree of airway obstruction. This maximum pressure level is determined during a one night CPAP titration study. However, pressure requirements vary with every patient and depend on the patient's physical condition (e.g. nasal congestion, alcohol effects, fatigue, sleep stage, body position, etc.). Therefore, the appropriate level determined during the sleep study usually is the maximum pressure required to overcome the most severe level of the upper airway obstruction during that one test.

These devices are deficient, since the maximum pressure with CPAP is not ideally suited to all occasions or every night. Because of the technical limitations, the pressure must be preset at a level higher than necessary during most of the sleep period. This creates various problems for the user. First, the long term effects of CPAP therapy are unknown, so it is desirable to keep the airway pressure as low as possible. Second, continuous high air flow leads to nasal dryness, discomfort, swallowing of air, etc., all of which tend to lower user compliance. Finally, the fact that CPAP pressure requirements change over time with changes in the patient's physiology, necessitates ongoing follow up and cost to assure that the optimal level of pressure is being delivered. Otherwise, the patient can be subjected to the risks of under-treatment or the hazards of over-treatment.

There have been several CPAP devices developed, such as the ones described in U.S. Pat. Nos. 5,117,819 to Servidio et al. and 5,199,424 to Sullivan et al., which attempt to improve user compliance by gradually increasing pressure from when the unit is first turned on, at a selected rate up to a predetermined and prescribed therapeutic level. This allows the patient to fall asleep at a more comfortable lower pressure. However, this prescribed pressure is still the highest pressure required to treat the worst case obstruction, the latter may only occur for a fraction of the total sleep period. Thus, the patient will be overtreated during much of this sleep period. Other patented CPAP devices, such as U.S. Pat. No. 5,239,995, to Estes et al. allows independent presetting of the inspiratory and expiratory prescribed pressures. This provides the patient with a more comfortable expiratory pressure, while the inspiratory pressure remains the same as with traditional CPAP. The patient however, will also be overtreated during the sleep period.

There are CPAP devices available, which automatically adjust CPAP pressure levels as a professional sleep technician would do during a traditional CPAP titration study. For example, U.S. Pat. No. 5,245,995 to Sullivan et al. discloses an apparatus which continuously senses a patient's breathing "patterns" through one or more sensors. When this device detects abnormal breathing "patterns", it increases the CPAP level to restore the patient's normal breathing, and prevent the collapse of the airway. This patent describes a microprocessor-based device that senses and evaluates breathing patterns over an extended period of time. The device accumulates, stores, analyses and retrieves data to determine the required pressure level changes. The Sullivan '995 patent, unlike the present invention, requires microprocessors, software and programming, which is complex, expensive and prone to problems such as the need to store data during any brief interruption of electrical power.

Sleep Apnea Syndrome (SAS) is defined as a critical reduction of air flow which lasts at least ten (10) seconds. Ten seconds is the minimum time required to cause significant blood oxygen desaturation and subsequent arousals from sleep. Therefore, the attempt to prevent all air flow reductions based upon past breathing patterns is unsound. For example, U.S. Pat. No. 5,245,995 describes a device that uses snoring and snoring patterns as an accurate parameter for detecting imminent apneic episodes. Once detected, said device increases the pressure to eliminate the snoring sound. However, not all people who snore have obstructive sleep apnea syndrome and not all snoring noises made by a patient with sleep apnea syndrome are associated with a detrimental reduction of air flow. In the latter situation, prior art devices may supply excessive air pressure to a "normally" functioning airway. The narrowing of the upper airway should be measured and only then treated with therapy. Until the optimal time is reached, positive airway pressure to the patient should be limited. U.S. Pat. No. 5,570,631 to Durkan shows a system which supplies discontinuous pulses or spikes of pressure therapy. Durkan however, fails to disclose any self-adjustability in the pressure supplied to the patient. Durkan also fails to address critical flow limitation problems which are characterized by a pressure drop of the same magnitude as a normal breath, but are of such short duration that the patient's inspiration volume is detrimentally reduced. Durkan's system uses a switch arrangement based on a static atmospheric threshold. Durkan's system also fails to compensate inhalation based upon the presence of a mask leak that would lower mask pressure below the static threshold. This reduced pressure in Durkin would be interpreted as an inhalation, thus preventing Durkan's system from properly administering pressure.

It is therefore an object of the present invention to provide a device which will interactively sense and respond on a breath-by-breath basis, and overcome detrimental air flow reductions in the airway of a patient.

It is a further object of the present invention to provide a respiratory device which will automatically self-adjust to a patient's diverse pressure requirements to effectively correct critical flow limitations.

It is yet a further object of the present invention to provide a respiratory device which generates the lowest possible mean pressure to avoid over-treating the patient with excessive air pressure.

It is still yet a further object of the present invention to provide a respiratory device which can automatically adjust its sensitivity to determine critical flow reduction in the presence of anticipated mask leaks.

BRIEF SUMMARY OF THE INVENTION

The present invention comprises a respiratory system for overcoming a critical airflow limitation as required by a patient connected to the system, comprising an airflow generating means; a delivery conduit in communication with the airflow generating means to direct a base level air pressure to the airway of the patient; an air sensing means arranged in fluid communication with the delivery conduit for detecting, on a continual basis, any changes in airflow to the airway of the patient; detection means arranged in communication with the air sensing means for continually providing a real time inspiratory breath attribute signal of the patient to a central circuit; reference signal means arranged with the sensing means for continually providing a real time dynamic tracking signal from the real-time inspiratory breath attribute signal; and decision means of the central circuit arranged to utilize the real-time inspiratory breath attribute signal and the real-time dynamic tracking means to identify a critical airflow limitation to the airway of the patient, the decision means being arranged with the airflow generating means to continuously increase air pressure from the airflow generating means to restore airway patency, and to instantaneously stop increasing and to begin decreasing air pressure, at a lesser rate and in a curvilinear fashion, upon detection of a normal inspiratory flow of air to the patient's airway. The invention also comprises the decision means being arranged to continuously increase air pressure from the airflow generating means when the real-time inspiratory breath attribute signal is less than the real-time dynamic reference tracking signal for a predetermined time duration, the decision means being arranged to stop increasing and begin decreasing, at a much lesser rate, the airflow generating means when the real-time inspiratory breath attribute signal is greater than the real-time dynamic reference tracking signal for a second predetermined minimum time duration. The invention includes detection means which differentiates between a normal and an abnormal single breath inspiratory flow attribute, and wherein the detection means utilizes a time based amplitude measurement to differentiate between the normal and abnormal breath attributes.

The invention also includes a first predeterminable time duration which is the maximum duration of time a patient can tolerate airflow limitation and not suffer detrimental blood oxygen de-saturation and physiological sleep disruptions therefrom, and a second predeterminable time duration which is the minimum duration of peak inspiratory flow required to be characterized as a normal inspiratory breath attribute. The invention further comprises further means for triggering the airflow generating means to stop increasing air pressure and begin decreasing, in a curvilinear fashion and at a much lesser rate, when the airflow generating means reaches the preset maximum pressure output level prior to the real-time single breath attribute signal being less than the real-time dynamic reference tracking signal for a third predeterminable minimum time duration, and including means for adjusting the magnitude of the base level pressure.

The invention includes a method of overcoming a constriction or critical airflow limitation of the airway of a patient attached to a , respiratory system, comprising the steps of: generating a constant low rate of air pressure from an airflow generator; directing a constant rate of air pressure through a delivery tube to a nasal mask worn by the patient; receiving a flow of air from the patient by a sensing means in the system; detecting a critical airflow limitation in the airway of the patient by sensing, on a breath to breath basis, a prolonged absence of a normal inspiratory flow signal; signaling the airflow generator to continuously increase the air pressure therefrom, upon detection of a restriction, so as to restore patency in the patient's airway; stopping the increasing air pressure to the patient upon sensing of a normal inspiration down the patient's now open airway; and triggering a subsequent signal to the generator to diminish the air pressure to the patient's now patent airway, to its prior constant low base level. The method also includes the decision means being arranged to continuously increase air pressure from the airflow generating means when the real-time inspiratory breath attribute signal is less than the real-time dynamic reference tracking signal for a predetermined time duration, the decision means being arranged to stop increasing and begin decreasing, at a much lesser rate, the airflow generating means when the real-time inspiratory breath attribute signal is greater than the real-time dynamic reference tracking signal for a second predetermined minimum time duration. The method includes a detection means which differentiates between normal and abnormal single breath inspiratory flow attributes, and when the first predeterminable time duration is the maximum duration of time a patient can tolerate airflow limitation and not suffer physiological sleep disruptions therefrom.

The method also includes determining when the second predeterminable time duration is the minimum duration of peak inspiratory flow required to be characterized as a normal inspiratory breath attribute.

The invention comprises a system for overcoming airway obstruction or restriction on demand, in a patient connected to the system, the system comprising: an airflow generating means, a delivery conduit in communication with the airflow generator and a mask worn by a patient so as to direct a flow of air to the patient, and an air sensing means in communication with the mask and adapted to rapidly change the air pressure from the airflow generating means upon the detection of a change in the airway of the patient wearing the mask. The system includes: a means for controlling the air pressure from the airflow generating means as it is sensed by the sensing means, and a mask which has a constant rate of air pressure directed to it, which rate is increased upon the detection of a prolonged airway obstruction or restriction from the patient wearing the mask.

The invention comprises a method of overcoming a restrictive or obstructive condition of the airway of a patient attached to a demand positive airway pressure system which system includes the steps of: generating constant air pressure from the airflow generator, directing constant air pressure from the airflow generator through a delivery tube to a nasal mask worn by the patient; directing a flow of air from the patient to a flow rate sensor; detecting an obstruction or restriction in the airway of the patient by sensing a prolonged absence or reduction of breath; and signaling the airflow generator to increase the air pressure therefrom to push open the obstruction or restriction in the patient's airway. The method also includes the steps of: continued sensing of the now restored breathing; and triggering a subsequent signal to the airflow generator to diminish the air pressure to the now unobstructed patient, to its normal constant low level.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
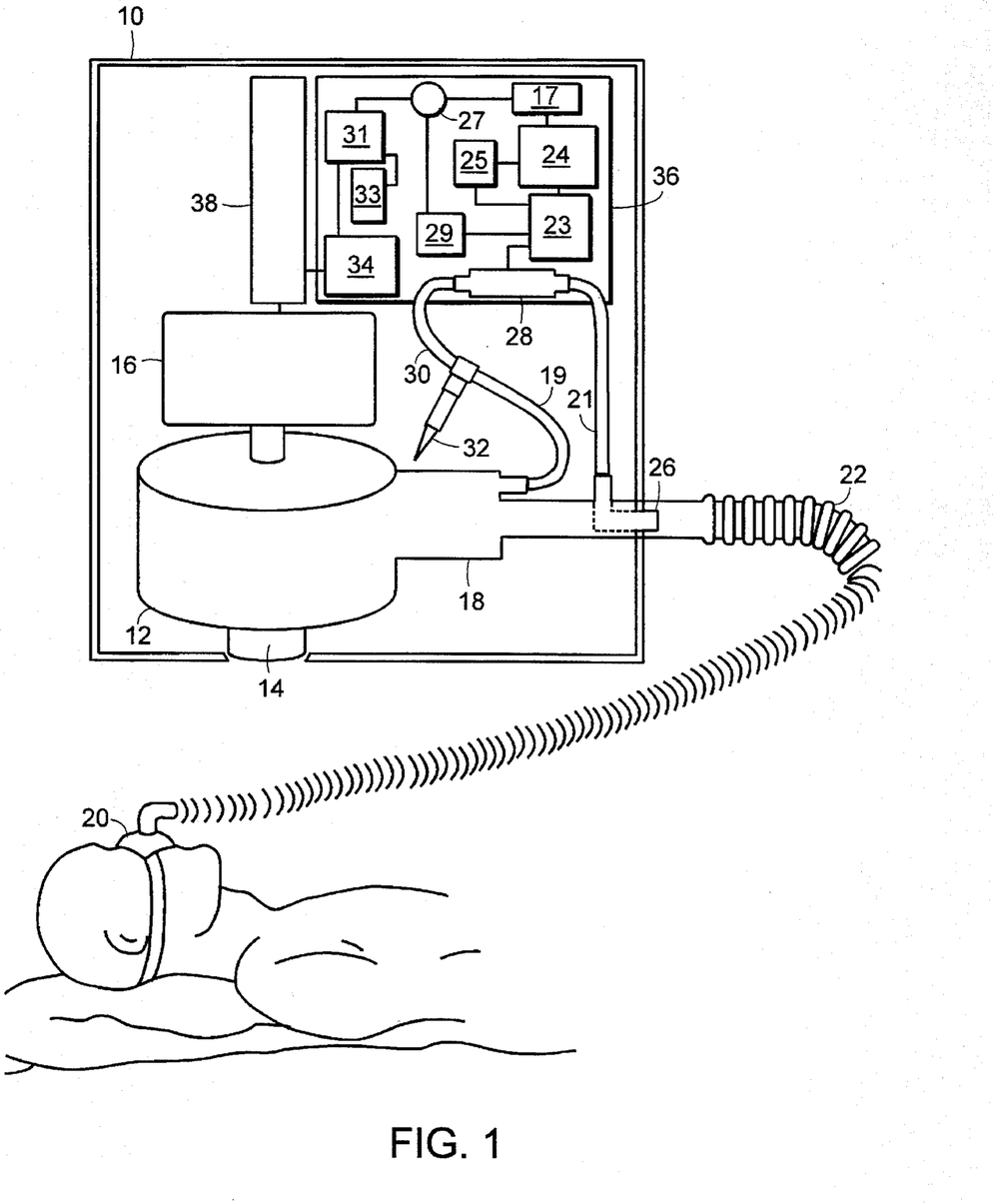
FIG. 1 is a plan view of the device, partly in section and partly in block diagram format.

Referring to the drawings in detail, and particularly to FIG. 1, there is shown a plan view and a schematic representation of a demand positive airway pressure system 10, which is utilized to show a device useful for restoring normal airflow in a patient with a critical airflow limitation.

This demand positive airway pressure system 10 comprises a blower unit 12 having an air intake port 14 or oxygen source. The blower unit 12 is rotatively powered by a variably adjustable electric motor 16 capable of continuous ramp up and ramp down. The blower unit 12 has an output port 18 which is in fluid flow communication with a nasal mask 20 through a wide bore delivery conduit 22. The delivery conduit 22, common in the field, is about ¾ of an inch in diameter.

A narrower sensing conduit 26 is also in fluid communication with the delivery conduit 22, as shown in FIG. 1. The sensing conduit 26 is also in communication with a sensor 28 through a first conduit 21, and a restrictor 32, which is a flow "restrictor", such as manufactured by Bird Precision Co. of Waltham, Mass., (which is a 0.040 inch flow restrictor), a barbed fitting having a central lumen for permitting controlled bleeding of flow of pressurized air from the downstream conduit 30. The restrictor 32 creates a lower pressure on the output side (conduit 30) of the flow sensor 28 to bias the flow sensor 28 for maximum sensitivity.

The downstream conduit 30 continues to be ducted through a biasing conduit 19 into the output port 18 of the blower 12. The conduit 19, 30 and 21 comprise a shunt in line with the flow sensor 28.

The flow sensor 28 thus is permitted to have a flow of air therethrough, because of the imbalance of air pressure between the first and downstream conduits 21 and 30 respectively. This is a precise way of measuring pressure within the mask 20. It is however, reading the pressure of the mask/patient, at or near the proximal end of the delivery conduit 22.

The flow sensor 28 comprises a portion of a circuit board 36, the components of which are shown in block form in FIG. 1. The circuit board 36 includes an electrical noise filtering circuit 23 comprised of a first high frequency polypropylene film capacitor shunted to ground, a series resistor followed by a second high frequency polypropylene film capacitor and a tantalum bead capacitor shunted to ground. The signal from the flow sensor 28, which is a voltage representation that reflects pressure and real-time changes thereto, is passed through the filtering circuit 23 and into an inhalation detection circuit 24. The inhalation detector circuit 24 comprises a high gain differential operational amplifier connected to a dynamic reference tracking circuit 25. The dynamic reference tracking circuit 25 is comprised of a voltage divider including a resistor/capacitor network, as shown in block form in FIG. 1.

A time delay feature is incorporated in the dynamic reference tracking circuit 25 through the use of two capacitors tied to ground. The output of this dynamic reference circuit 25 based on the input of the flow sensor 28, provides a reference voltage signal "R" that is slightly below the airflow sensor 28 voltage output, and lags the real time changes as communicated through the sensing and first conduits 26 and 21, and generated by the airflow sensor 28. The dynamic reference circuit 25 feeds a signal to a negative input on the differential operational amplifier of the inhalation detection circuit 24. The filtered signal from the electrical noise filtering circuit 23 drives the positive input of the operational amplifier of the inhalation detection circuit 24. The operational amplifier of the inhalation detector circuit 24 compares the real time filtered sensor output to the dynamic reference tracking generated by the dynamic reference tracking circuit 25. When the signal from the flow sensor 28, (as filtered by the electrical noise filtering circuit 23), is higher than the dynamic reference signal, the output of the differential operational amplifier is low, or a "logical" zero.

Figure 2A:
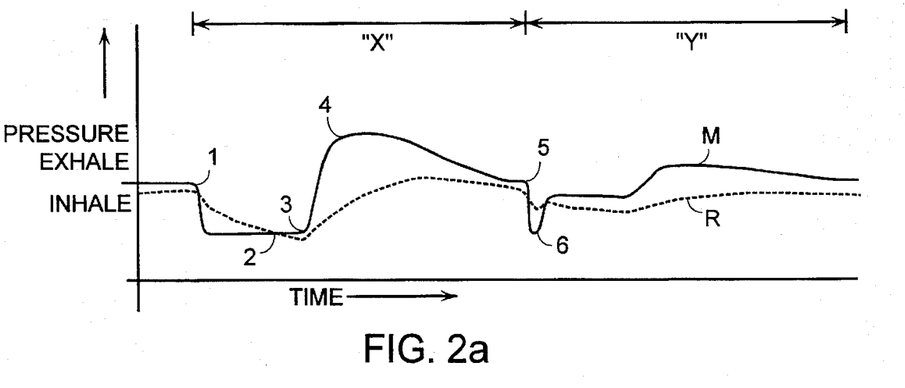
FIG. 2a is a graph which represents the patient mask pressure and the dynamic reference signal as a function of time.
Figure 2B:
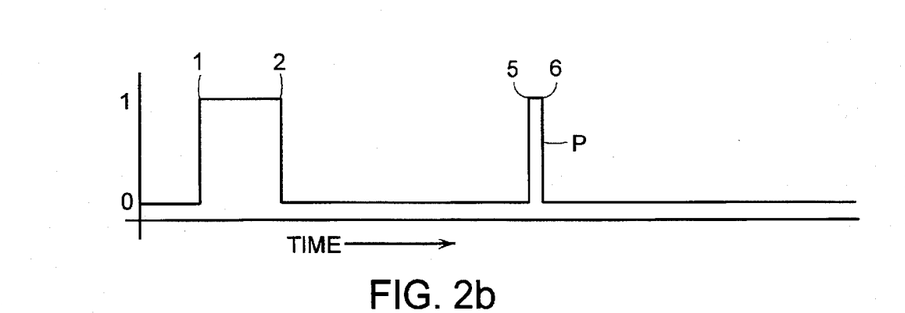
FIG. 2b is a graph which shows a representation of the signal of the inhalation detector with respect to time.

When the signal from the flow sensor output 28, (as filtered by the electrical noise filtering circuit 23), drops below the dynamic reference tracking signal, the output of the differential operational amplifier goes high or a "logical" one. The response of this inhalation detector circuitry, is shown in FIGS. 2a and 2b.

In the presence of a mask leak, a signal from the flow sensor 28 will be reduced in proportion to the amount of air leaking. The voltage divider in the aforementioned dynamic reference tracking circuit 25 automatically reduces the reference tracking signal "R" proportionately, in order to maintain the same level of inhalation sensitivity.

An antifalsing circuit 17 is connected to the output of the inhalation detection circuit 24. The antifalsing circuit 17 comprises a series resistor and 10 micro farad capacitor shunted to ground, as shown in block form in FIG. 1. The resistor and capacitor in this circuit 17 slow down the output of the differential operational amplifier in the inhalation detection circuit 24 to prevent short duration pulses, which characterize "critical flow limitations" (reduced inhalation), from being sensed as normal inhalation.

A timing circuit 27, which comprises a NE556 one-shot circuit, in a monostable configuration, acts to time the duration between "logical" ones from the output of the antifalsing circuit 17. The timing circuit 27 sends its output to a selector circuit 31. The selector circuit 31 is for example, a Gordos, model 836C-1 relay, driven by a NPN transistor type 2N2102. The selector circuit 31 selects one of two reference voltages generated in the output reference circuit 33, and sends it to a pressure decay circuit 34 and then into a speed control unit 38. The output reference circuit 33, as shown in block form, in FIG. 1, is comprised of a multi turn 10K Ohm trimpot in series with a 10K Ohm fixed resistor, connected between a positive voltage source and ground. A 10 micro farad electrolytic capacitor is connected from the voltage tap on the voltage divider circuit in the output reference circuit 33 to provide stable voltage for transmission to the pressure decay circuit 34.

The pressure decay circuit 34, is comprised of an operational amplifier, for example, a National Semiconductor LM-358, which charges a 10 micro farad electrolytic capacitor through a signal diode, for example a type 1N 4148, and a 100K Ohm multi-turn trimpot.

A 4.7M Ohm fixed resistor is placed in series with a 5M Ohm multi-turn trimpot. This resistor combination is placed in parallel with the 10 micro farad electrolytic capacitor, to provide an adjustable bleed down of the resulting voltage. This voltage is then sent to a second operational amplifier, such as a National Semiconductor d-358, to provide the needed current to drive the blower speed control unit 38.

The blower speed control unit 38, part of a system, which includes the blower unit 12 and blower motor 16, is manufactured for example by Ametek Lamb Electric Division of Kent, Ohio.

A maximum pressure detector 29 is in communication with the output line of the noise filter 23 and the input line of the timing circuit 27. The pressure detector circuit 29 is comprised of a high gain differential operational amplifier, for example, a National Semiconductor LM-339, with a reference voltage applied to negative input, as shown in block form in FIG. 1. The voltage is adjusted during assembly/testing so that the output of the high gain operational amplifier goes "high" or logical one, when a maximum pressure of 20 cm. of water is reached. The output of the high gain differential operational amplifier is sent to the timing circuit 27 to reset the NE 556 timer and select the low output reference voltage and returns the blower unit 12 to its base level setting of 2.5 cm of water, through the components previously described.

Referring again to FIG. 2a, mask pressure as a function of time is shown, for a normal breath duration "X", and a reduced duration "Y". This reduced breath is the graphical representation of the "critical flow limitation". This mask pressure, in cm. of water, is measured by the flow sensor 28 through the first and sensing conduits 21 and 26. Pressure is shown on the vertical axis, whereby increased pressure is shown in the "up" direction and reduced pressure is shown in the "down" direction. At point 1 in FIG. 2a, the patient begins a normal inhalation. The resultant flow reduces the mask pressure so as to pull the sensor signal "M" significantly below the dynamic reference tracking signal "R". At point 2 of FIG. 2a, while the patient continues to inhale, the dynamic reference tracking signal "R" drops below the airflow sensor signal "M".

The capacitors in the dynamic reference circuit 25 provide the time lapse, to establish the slow rate of change in the dynamic reference tracking signal "R". The voltage divider of the dynamic reference tracking circuit 25 provides the force to drive the dynamic reference tracking signal "R" below the airflow sensor signal "M".

At the end of the patient inhalation cycle, indicated as point 3, in FIG. 2a, the voltage divider in the dynamic reference circuit 25 has returned the dynamic reference tracking signal "R" well below the airflow sensor signal "M".

When the patient begins to exhale, the airflow sensor signal "M" rapidly rises to a peak, indicated at point 4, in FIG. 2A. The capacitors in the dynamic reference circuit 25 do not allow the dynamic reference tracking signal "R" to increase at the same rate as the airflow sensor signal "M".

For purposes of example, the next inhalation of the patient shown is not a full inhalation and represents a critical flow limitation that begins at point 5 in FIG. 2A. The airflow sensor signal "M" is shown being pulled below the dynamic reference tracking signal R for a greatly reduced period of time, at point 6, because the reduced pressure during inhalation allows the patient's airway to constrict. It is to be noted that the dip in amplitude at point 6 is the same as that of a normal breath. Once the airway has narrowed, as at point 6, the airflow sensor signal "M" rises because the patient no longer draws in air (inhales sufficient air) to pull the airflow pressure signal "M" down. The remaining portion of the curve represents the reduced volume of air taken in by the patient. The two breaths shown may be followed by a repeat of either of them.

In FIG. 2b, there is shown a representation of the output of the inhalation detector 24 with respect to time, corresponding to the time base, as identified in FIG. 2a.

In FIG. 2b, the inhalation signal is shown, which is generated by the high gain differential amplifier of the inhalation detection circuit 24. The output of this amplifier goes from logical zero to logical one at point 1 on FIG. 2b, which corresponds to the location of point 1 on FIG. 2a.

The output of this amplifier remains at logical one until the signal reaches point 2, which corresponds to the location of point 2 on FIG. 2a. Then the output of the amplifier switches to logical zero at this time, and remains there until the sensor signal "M" drops below the dynamic reference signal "R", as indicated at the corresponding location of point 5 on FIG. 2a.

The output of the amplifier remains at logical one until the sensor signal "M" rises above the dynamic reference signal "R", as indicated at the location of point 6, in FIGS. 2a and 2b. At that time, the output of the amplifier drops to logical zero and remains there until patient inhalation is detected by the airflow sensor. FIG. 2b shows the false inhalation detection, corresponding to the time between points 5 & 6 of FIGS. 2a and 2b, which is a very short time duration (on the order of a tenth of a second).

Figure 2C:
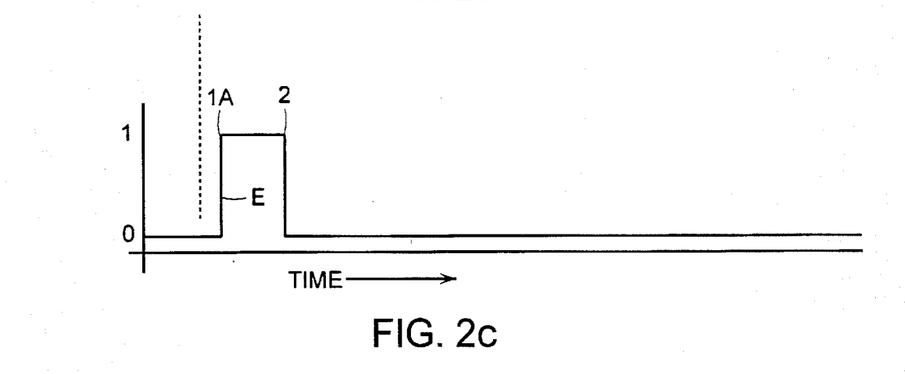
FIG. 2c is a graph which shows a representation of the inhalation detector with the antifalsing circuit included therewith.

FIG. 2C shows how the time delay in the antifalsing circuit 17 modifies the signal sent to the timing circuit 27 by delaying the leading edge "E" of the square wave and totally eliminating the false inhalation detection wave "P" indicated in FIG. 2b.

At the location of point 1 in FIG. 2C, which corresponds to point 1 on the time line for FIGS. 2a and 2b, the output of the antiraising circuit is logical zero because of the capacitance causing the delay in the antifalsing circuit.

A point, indicated on the time scale, as "1A", represents the output of the antifalsing circuit changing to a logical one.

This logical one resets the timer circuit 27 and keeps the blower 12 at its base level.

At a location which is an approximate correspondence to the location of point 2 on FIGS. 2a and 2b, the output of the antifalsing circuit returns to logical zero and allows the timer 27 to begin counting until the next inhalation is detected, thus establishing a breath to breath analysis by the system 10, upon the patient attached thereto.

FIGS. 2a, 2b and 2c represent "inhalation" which is the breath attribute being monitored on a single breath basis by the present invention.

The operation of the system is based on the definition of sleep apnea syndrome (SAS). A patient has an apneic event if breathing ceases or is critically reduced for at least 10 seconds. The system 10 treats sleep apnea syndrome (SAS) with a continuously increasing airway pressure to restore airway patency. The system 10 supplies the patient with a constant low pressure (e.g. 2.5 cm of water) flow of air during periods of normal breathing. The system 10 determines the time interval from breath to breath of the patient during periods of normal breathing using the flow sensor 28. Should the patient develop critical flow limitation for a prolonged period (e.g. 8 seconds), the system 10 will respond by continuously increasing pressure to the patient to restore airway patency. The system 10 can reach maximum pressure, which is about 20 cm of water, within 10 seconds of the last normal breath. This pressure is generally accepted as the maximum pressure required to treat the most severe cases of SAS.

The airflow sensor 28 and associated circuitry detects normal inhalation. The system 10 then times the interval between inhalations to determine if response is necessary. The breath to breath sensing and timing could be accomplished with exhalation or with changes between inhalation and exhalation. The key principle is diagnosing and treating "critical flow limitation", regardless of airway pressure.

Figure 3:
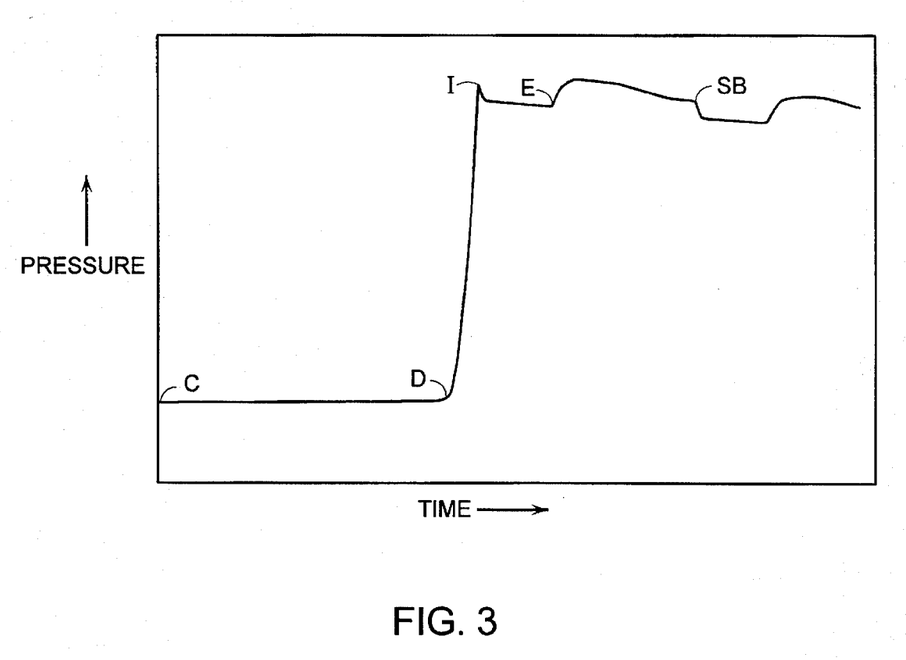
FIG. 3 is a graph which shows a representation of how the present invention limits airway pressure based upon patient inhalation.

The system 10 responds to prolonged critical flow limitations (greater than 8 seconds), by increasing pressure in a continuous manner up to a point of normal inhalation as determined by the patient's physiological response, whereupon the system 10 begins a gradual ramp down in pressure over an extended period of time (e.g. at least about 30 seconds) to reach its constant low pressure base level of 2.5 cm of water, as shown in FIG. 3, which decline in pressure is controlled by the pressure decay circuit 34, as shown in FIG. 1. The blower unit 12 and the motor 16 of the system 10 can increase from the base output of approximately 2.5 cm of water to approximately 20 cm of water in less than 2 seconds. The system 10 thus responds if it fails to detect a normal inhalation within about 8 seconds. This response allows the system 10 to restore airway patency in less than 10 seconds; thereby preventing an apneic event.

The system 10 maintains an elevated pressure during the gradual ramp down, as aforementioned, to insure that the patient's airway remains patent after the restriction or flow limitation has been overcome, and to permit the patient to continue normal breathing. The inhalation detector 24 is able to detect inhalation while the blower unit 12 is increasing the output from 2.5 to 20 cm of water. The speed of the inhalation detector 24 allows the system 10 to administer only the appropriate pressure to restore the airway patency. The inhalation detector 24 can stop the blower unit 12 from acceleration, and begin the gradual aforementioned ramp down of pressure at output levels corresponding to where the patient has a normal inhalation between the base output and the maximum output, as shown for example at the location "I" in FIG. 3.

FIG. 3 is a graphical representation of the pressure changes in the mask 20, with the "pressure" shown on the vertical axis, and the "time" on the horizontal axis. Point "C" on the curve represents the onset of critical flow limitation, and point "D" on the curve shows the beginning of pressure increase in the system (8 seconds after point "C"). The maximum point, shown at the location "I" shows the immediate pressure drop associated with a normal inhalation. The maximum pressure reached is limited by the spontaneous inhalation of the patient. The normal inhalation continues until point "E" on the curve of FIG. 3, at which point the pressure begins to rise as a result of patient exhalation. A subsequent breath begins at the point marked "SB" during the gradual ramp down in pressure. This curve of FIG. 3 clearly depicts how the system 10 limits a specific pressure increase to that required by the patient's immediate physiological needs.

In operation, the system 10 will generate a pressure rise only to the pressure required to restore normal breathing. It is important to use a dynamic reference signal to detect inhalation of a patient on positive pressure therapy because the patient can not easily create inhalation pressure below ambient. The pressure required to restore airway patency in any given patient will be different at any given time, and the dynamic reference circuit 25 of the present invention is required to detect these critical flow limitations while the patient is on positive airway pressure therapy.

When normal breathing is re-established, (continued normal inhalation in less than 8 second intervals), the system 10 will return to the comfortable low pressure base output (eg. 2.5 cm. of water).

The system 10 adds an additional feature that prevents the unit from dwelling at maximum output in the event that breathing cannot be re-established.

This automatic kick down circuitry uses a fixed reference of about 20 cm of water to reset the timer and reduce blower output.

Thus what has been shown is a novel system for restoring airway patency, breath to breath, to a patient attached to the system.

We claim:

1. System for treating critical airflow limitation in a patient, the system comprising:

means for generating a pressurized gas flow;

a conduit in fluid communication with said generating means for delivering the gas flow to an airway of a patient;

a flow sensor in fluid communication with the gas flow for generating a breath signal having an amplitude representative of patient breathing; and circuitry for regulating the gas flow responsive to said breath signal by controlling the generating means, said circuitry comprising:

a) means for providing a base level pressure of gas flow;

b) means for monitoring the breath signal to identify a normal breath attribute sensed by said flow sensor;

c) means for monitoring the breath signal to identify a critical airflow limitation;

d) means for continuously and non-incrementally increasing pressure of the gas flow to no greater than a preselected maximum system pressure upon detection of a critical airflow limitation indicated by absence of a normal breath attribute in a single breath in said breath signal within a predetermined period from detection of a normal breath attribute; and e) means for decreasing pressure of the gas flow upon detection of restored breathing indicated by presence of said normal breath attribute in a single breath in said breath signal, said normal breath attribute corresponding to a time-based amplitude in a single breath.

2. The invention according to claim 1 wherein the normal breath attribute comprises a minimum duration of peak inspiratory flow from initiation of inspiration.

3. The invention according to claim 2 wherein the circuitry comprises:

a reference circuit for creating a reference signal which lags the breath signal in amplitude and time; and a detection circuit for detecting the initiation of inspiration at crossing of the breath signal with the reference signal.

4. The invention according to claim 3 wherein the breath signal corresponds to gas flow pressure; and breath signal amplitude corresponding to the minimum duration of peak inspiratory flow is less than amplitude of the reference signal.

5. The invention according to claim 2 wherein the circuitry comprises;

a timing circuit for measuring said predetermined period; and an antifalsing circuit for resetting the timing circuit upon detection of a breath having the normal breath attribute.

6. The invention according to claim 1 wherein the predetermined period is less than an apneic event duration of at least ten seconds.

7. The invention according to claim 1 wherein:

the generating means includes an output port;

the delivery conduit has a proximal end in fluid communication with the output port and a distal end in fluid communication with the patient airway; and the flow sensor is disposed in a gas circuit disposed between the output port and the delivery conduit proximal end.

8. A method for treating critical airflow limitation in a patient comprising the steps of:

supplying a pressurized gas flow at a base level pressure to an airway of a patient;

sensing and generating a breath signal having an amplitude representative of patient breathing by sensing said gas flow;

providing circuitry for regulating the gas flow responsive to said breath signal by controlling the supplying of the pressurized gas flow, wherein said circuitry comprises:

a) means for providing a base level pressure of gas flow;

b) means for monitoring the breath signal to identify a normal breath attribute sensed by said flow sensor; and c) means for monitoring the breath signal to identify a critical airflow limitation;

continuously and non-incrementally increasing pressure of the gas flow to no greater than a preselected maximum system pressure upon detection of critical airflow limitation indicated by absence of a normal breath attribute in a single breath in said breath signal within a predetermined period from detection of a normal breath attribute; and decreasing pressure of the gas flow upon detection of restored breathing indicated by presence of said normal breath attribute in a single breath in said breath signal, said normal breath attribute corresponding to a time-based amplitude in a single breath.

9. The method according to claim 8 wherein:

the normal breath attribute comprises a minimum duration of peak inspiratory flow from initiation of inspiration.

10. The method according to claim 9 wherein initiation of inspiration is established by the circuitry:

creating a reference signal which lags the breath signal in amplitude and time; and detecting crossing of the breath signal with the reference signal.

11. The method according to claim 9 further comprising the steps of:

measuring said predetermined period using a timing circuit; and restarting said predetermined period upon detection of a breath having the normal breath attribute.

* * * * *